US011259702B2

(12) United States Patent
Yamada

(10) Patent No.: US 11,259,702 B2
(45) Date of Patent: Mar. 1, 2022

(54) FIBER OPTIC IMAGING PROBE HAVING CLADDING MODE PULLBACK TRIGGER, AND CONTROL METHOD THEREFOR

(71) Applicant: Canon U.S.A., Inc., Melville, NY (US)

(72) Inventor: Daisuke Yamada, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 985 days.

(21) Appl. No.: 15/689,561

(22) Filed: Aug. 29, 2017

(65) Prior Publication Data

US 2019/0059734 A1 Feb. 28, 2019

(51) Int. Cl.
*A61B 5/00* (2006.01)

(52) U.S. Cl.
CPC .......... *A61B 5/0066* (2013.01); *A61B 5/0035* (2013.01); *A61B 5/0071* (2013.01); *A61B 5/6852* (2013.01); *A61B 5/0086* (2013.01)

(58) Field of Classification Search
None
See application file for complete search history.

(56) References Cited

U.S. PATENT DOCUMENTS

| 7,382,464 | B2* | 6/2008 | Everett | A61B 3/102 356/479 |
|---|---|---|---|---|
| 7,447,408 | B2 | 11/2008 | Bouma et al. | |
| 8,412,312 | B2 | 4/2013 | Judell et al. | |
| 8,792,757 | B2 | 7/2014 | Boudoux et al. | |
| 9,295,391 | B1 | 3/2016 | Tearney | |
| 9,332,942 | B2 | 5/2016 | Jaffer et al. | |
| 9,526,424 | B2 | 12/2016 | Judell et al. | |
| 9,557,154 | B2 | 1/2017 | Tearney et al. | |
| 9,610,064 | B2 | 4/2017 | Adler et al. | |
| 10,285,568 | B2* | 5/2019 | Tearney | A61B 1/00082 |

(Continued)

FOREIGN PATENT DOCUMENTS

| JP | 2010-158343 A | 7/2010 |
|---|---|---|
| WO | 2016182164 A1 | 11/2016 |

OTHER PUBLICATIONS

Lanzer, P., "Catheter-Based Cardiovascular Interventions: A Knowledge-Based Approach", pp. 364.

(Continued)

*Primary Examiner* — Luther Behringer
(74) *Attorney, Agent, or Firm* — Canon U.S.A., Inc., IP Division

(57) ABSTRACT

An optical coherence tomographic (OCT) system includes a sample arm, a reference arm and an OCT probe. The probe irradiates a bodily lumen and a fluid contained within the bodily lumen with light of a sample beam transmitted through a double-clad fiber (DCF). A first detector detects light of a reference beam and light reflected from the bodily lumen and propagated through the core of the DCF to generate OCT interference signals. Light backscattered by the bodily lumen and by the fluid contained in the bodily lumen is propagated through a cladding of the DCF and detected by a second detector to generate an intensity signal. A processor analyzes the intensity signal, and triggers a pullback of the probe and initiates recording of OCT images of the bodily lumen in response to the intensity the backscattered light reaching a predetermined threshold value.

12 Claims, 11 Drawing Sheets

(56) References Cited

U.S. PATENT DOCUMENTS

| | | | |
|---|---|---|---|
| 2006/0158655 A1* | 7/2006 | Everett | A61B 3/102 |
| | | | 356/479 |
| 2009/0323076 A1 | 12/2009 | Li et al. | |
| 2011/0071405 A1 | 3/2011 | Judell et al. | |
| 2011/0299091 A1 | 12/2011 | Yun et al. | |
| 2012/0004506 A1* | 1/2012 | Tearney | A61B 1/0008 |
| | | | 600/116 |
| 2012/0022360 A1 | 1/2012 | Kemp | |
| 2014/0180083 A1 | 6/2014 | Hoseit | |
| 2014/0180133 A1 | 6/2014 | Brennan et al. | |
| 2014/0301620 A1 | 10/2014 | Tearney et al. | |
| 2015/0366536 A1 | 12/2015 | Courtney et al. | |
| 2016/0007837 A1 | 1/2016 | Hiltner et al. | |
| 2016/0228071 A1 | 8/2016 | Wang et al. | |
| 2016/0335766 A1 | 11/2016 | Ambwani et al. | |
| 2017/0135584 A1 | 5/2017 | Tearney et al. | |
| 2017/0196459 A1 | 7/2017 | Lam et al. | |
| 2017/0209049 A1 | 7/2017 | Wang et al. | |

OTHER PUBLICATIONS

Hariri, L.P., et al, "An automatic image processing algorithm for initiating and terminating intracoronary OFDI pullback". Biomed Opt Express, Sep. 1, 2010, pp. 566-573, vol. 1, No. 2.

Scollaro, L., et al, "Molecular imaging needles: dual-modality optical coherence tomography and fluorescence imaging of labeled antibodies deep in tissue", Biomed Opt Express, May 1, 2015, pp. 1767-1781, vol. 6, No. 5.

Su, J., et al, "Real-time swept source optical coherence tomography imaging of the human airway using a microelectromechanical system endoscopy and digital signal processor", J. Biomed Opt., May-Jun. 2008, vol. 13, No. 3.

Suter, M. J., et al, "Optimizing flushing parameters in intracoronary optical coherence tomography: an in vivo swine study", Int. J. Cardiovasc Imaging, 2015, pp. 1097-1106, vol. 31.

Kashiwagi, M., et al, "Optical Coherence Tomography in Coronary Artery Disease: Toward Sub Cellular Imaging", Austin J. Clin Cardiolog, 2014, vol. 1, No. 3.

Madore, W., et al, "Asymmetric double-clad fiber couplers for endoscopy", Optics Letters, Nov. 1, 2013, pp. 1514-4517, vol. 38, No. 21.

Yelin, D., et al, "Double-clad fiber for endoscopy", Optics Letters, Oct. 15, 2004, pp. 2408-2411, vol. 29, No. 20.

Sharma, U., et al, "Fiber Optic Interferometric Devices", Fiber Optic Sensing and Imaging, 2013, pp. 29-53.

Keiser, G., et al, "Review of diverse optical fibers used in biomedical research and clinical practice", Journal of Biomedical Optics, Aug. 2014, vol. 19, No. 8.

Volcano, Volcano Revo Option, Operator's Manual, Software Version Level 3.3.X.

\* cited by examiner

Illuminating, core or single-mode light – – – – – – ▶
Backscattered, clad or multi-mode light ◀– – – – – –

FIBER OPTIC IMAGING PROBE HAVING CLADDING MODE PULLBACK TRIGGER, AND CONTROL METHOD THEREFOR

BACKGROUND

Field

The disclosure of this patent application relates generally to optical imaging, and in particular it relates to medical optical imaging of bodily lumens wherein a fiber optic imaging apparatus uses a cladding mode for trigger of lumen clearance, and control methods therefor.

Related Art

Fiber optic probes, such as catheters and endoscopes, have been developed to access and image internal organs of humans and animals, and are now commonly used in various medical fields. For example in cardiology, fiber based optical coherence tomography (OCT) has been developed to see depth-resolved images of vessels with a catheter. The catheter, which generally comprises a sheath, a coil and an optical probe, is navigated to a coronary artery, by manual or automatic control. In order to acquire cross-sectional images of tubes and cavities such as vessels, esophagus and nasal cavity, generally referred to as "bodily lumens", the optical probe is rotated with a fiber optic rotary joint (FORJ). In addition, the optical probe is simultaneously moved (translated) longitudinally during the rotation so that images are obtained in a helical scanning pattern. This longitudinal movement is most commonly performed by mechanically pulling the tip (distal end) of the probe back towards the proximal end and therefore this process is referred to as a "pullback" operation.

Imaging of coronary arteries by intravascular OCT systems allows the inspection of blood vessel sizes and plaques from inside of vessels. However, blood cells strongly scatter the OCT light. Therefore, blood clearance is necessary to see inside the lumen. Contrast agents, saline solution, dextran, or other liquids are flushed to clear the blood cells prior to pullback. Alternatively, blood clearance can be achieved by the use of a balloon filled with an optically clear medium, such as radio-opaque contrast, saline solution, or pumped air. The balloon may surround the region of the catheter where light exits from (and returns to) the imaging probe. In any case, when blood cells are cleared from around the imaging probe, the system needs to record OCT images with a pullback in a short amount of time.

Conventionally, manual pullback initiation and termination has been common practice based on real-time image processing using a second imaging modality. In addition, automated pullback initiation and termination has been proposed based on real-time image processing of acquired OCT images. However, extensive data analysis is necessary to perform accurate real-time image processing prior to initiating automated pullback.

For example, Suter et al., in a non-patent literature (NPL) document entitled "Optimizing flushing parameters in intra-coronary optical coherence tomography: an in vivo swine study", Springer Science, 2015, describes the need to analyze each frame of acquired OCT images to determine whether (a) blood obscures visualization of the vessel wall, (b) vessel lumen is visible, (c) diagnostic quality images of the artery wall are acquired, or (d) no blood is visible in the artery lumen. This process requires substantial computing power and processing time. Similarly, Hariri et al., in an NPL article entitled "An automatic image processing algorithm for initiating and terminating intracoronary OFDI pullback", Biomedical Express, Vol. 1, No. 2, September 2010, disclosed certain image processing techniques to determine when the OCT image contains a clear, diagnostic-quality view of the artery wall, as opposed to a blood obstructed view, to generate a control signal in real-time to start and stop pullback and digital data recording.

In another example, Judell et al., (U.S. Pat. No. 8,412, 312) describes a computer-implemented method of analyzing one or more frames of optical coherence tomography data collected from a vessel, determining if a blood clearing state has occurred, and generating a trigger signal for pullback and image recording, in response to the blood clearing state. Judell endeavors to reduce the amount of processing time to detect a flush clearing state based on OCT data of one or more frames of OCT images. However, this computer-implemented method similarly requires computational power and time to analyze the OCT images and determine when sufficient blood clearance has been achieved. In particular, Judell describes the flush clearing detection method requires time for processing each image frame prior to generating the trigger signal.

Furthermore, Courtney et al., (US 20150366536) discloses a system that uses two imaging modalities to perform a method where, during a first pullback operation, images obtained from a first imaging modality are processed in real-time to identify a region of interest. If the images obtained from the first imaging modality identify a region of interest, a flush operation is performed while recording images with a second imaging modality during a second pullback operation. According to Courtney, the first imaging modality must compatible with the presence of an intraluminal medium to obtain images that are recorded and processed to identify regions of interest and then start a flush operation. Therefore, this method and system not only requires processing time to identify regions of interest, but it also requires a modality able to obtain images in the presence of an intraluminal medium.

However, as long as the detection and processing of diagnostic-quality images is required to trigger pullback and image recording, it remains difficult to achieve high-speed real-time image acquisition without delay. Therefore, the need to acquire an adequate amount of imaging data in a minimum amount of time after the lumen starts to clear remains unsolved.

SUMMARY

The present patent application aims to improve on the above-described state of the art. According to an aspect of the present application, a system detects blood clearance and automatically starts pullback and image recording based on detection of light scattered by blood cells near the distal end of an OCT probe. This method does not require computing power or processing time to detect and process diagnostic-quality images because a trigger signal is generated based on the intensity of the detected signal. Therefore this novel technique can achieve high-speed acquisition in real-time.

According to at least one embodiment, an optical coherence tomographic (OCT) system includes a sample arm, a reference arm, and an OCT probe. The probe irradiates a bodily lumen and a fluid contained within the bodily lumen with light of a sample beam transmitted through a double-clad fiber (DCF). A first detector detects light of a reference beam and light reflected from the bodily lumen and propagated through the core of the DCF to generate OCT interference signals. Light backscattered by the bodily lumen and BY the fluid contained in the bodily lumen is propagated through a cladding of the DCF and detected by a second detector to generate an intensity signal. A processor analyzes the intensity signal, and triggers a pullback of the probe and initiates recording of OCT images of the bodily lumen in response to the intensity the backscattered light reaching a predetermined threshold value.

Further features and advantageous of the invention will become apparent to those skilled in the art from the following description of exemplary embodiments with reference to the attached drawings.

DETAILED DESCRIPTION

Figure 1:
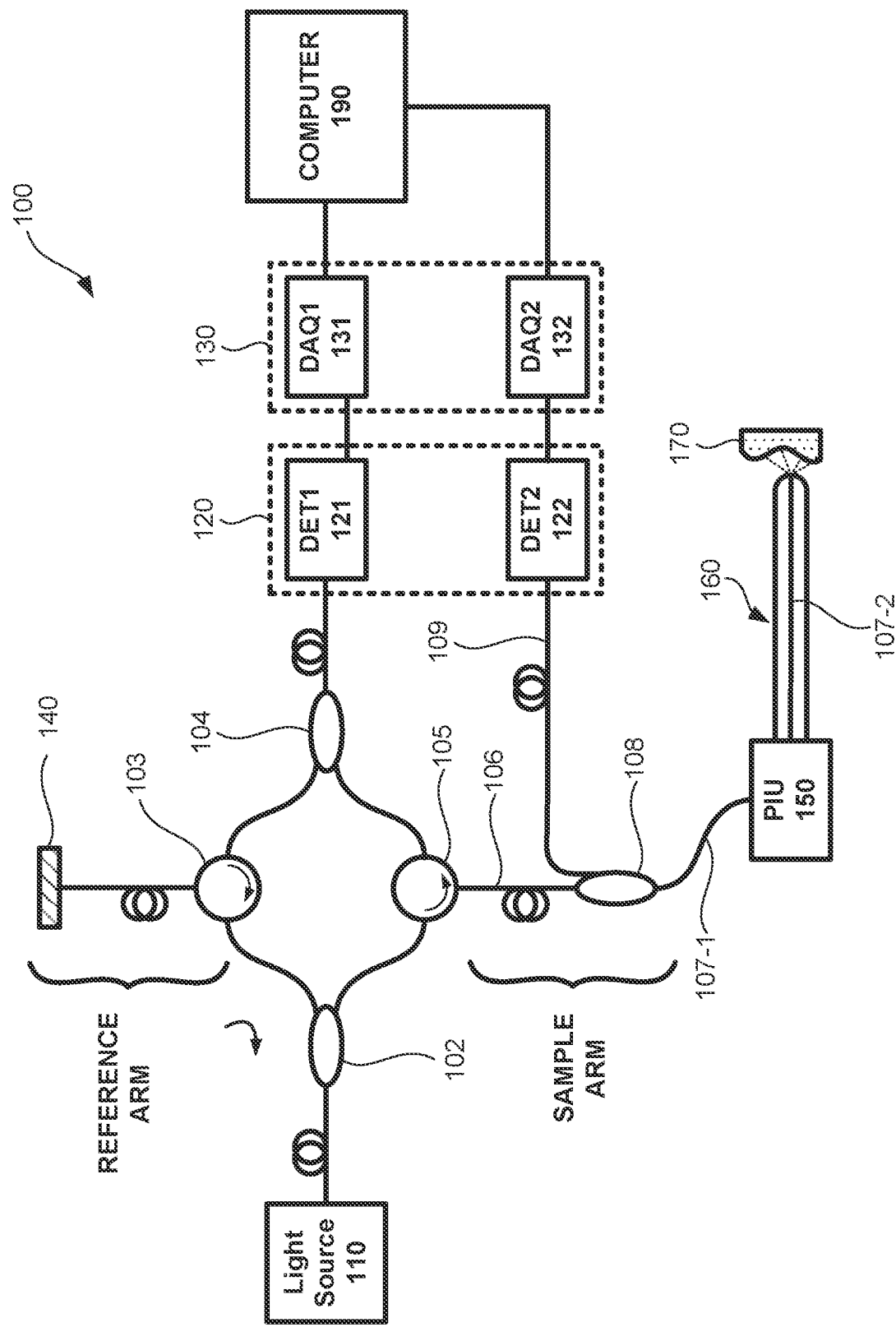
FIG. 1 is a functional block diagram of an OCT imaging system according to some embodiments.

In the following description, reference is made to the accompanying drawings which are illustrations of embodiments in which the disclosed invention may be implemented and practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage devices such as a magnetic or optical disk and disk drive for storing information and instructions, an optional user output device such as a display device (e.g., a monitor) for displaying information to a user, an optional user input device including alphanumeric and function keys (e.g., a keyboard) for communicating information and command selections to the processor, and an optional user input device such as a pointing device (e.g., a mouse) for communicating user input information and command selections to the processor.

As will be appreciated by those skilled in the art, the present examples may be embodied as a system, method or computer program product. Accordingly, some examples may take the form of an entirely hardware embodiment, an entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any non-transitory tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that when executed by a computer or other programmable data processing apparatus causes the computer or processing apparatus to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without departing from structural or functional meaning.

Exemplary embodiments are described below in more detail with reference to the several drawings where like reference numerals refer to like parts. FIG. 1 is/illustrates a block diagram of an exemplary OCT system 100.

Broadly, according to some embodiments, an OCT system comprises a catheter having an optical probe, which is made of an optical fiber with at least 2 clads (DCF). The optical probe serves to illuminate and collect light from a sample with a single fiber. Light 1 illuminates the sample using the optical probe. Light 2 (OCT light) is collected from different depths of the sample by the optical probe and propagated to a first detector through the core of the DCF to generate OCT images. Light 3 (scattered light) is collected by the optical probe from the sample surface and from scattering media, and is propagated to a second detector through the clad of the DCF. The intensity of light 3 is a function of a distance from the optical probe to the sample surface. The collected light 2 and light 3 are separated with a coupler to propagate to the first and second detectors. Light 1, 2 and 3 are all the same wavelength. A trigger signal is generated based on detected intensity of light 3 signals in order for a processor to control an operation of the catheter and record OCT images.

More specifically, FIG. 1 illustrates an exemplary interferometric OCT system 100 that can be applied as an intravascular OCT system for imaging of coronary arteries or other bodily lumens. It should be noted that the interferometric OCT system 100 may also be adapted to be used as an intralumen imaging system in a fluoroscopy imaging modality. In addition, the interferometric OCT system 100 may be applicable for esophageal imaging when combined with balloon catheters. As depicted in FIG. 1, the OCT system 100 includes an interferometer having a sample arm and a reference arm, a light source 110, a detector unit 120, data acquisition electronics 130, and a data processing computer 190. The sample arm includes a patient interface unit (PIU) 150, an OCT probe 160. The OCT probe 160 (catheter) is connected to the sample arm via the patient interface unit (PIU) 150. Light from the coherent light source 110 (e.g., a laser source) is guided through the sample arm to a sample 170, and through the reference arm to a reflector 140, to thereby generate OCT interference patterns.

Specifically, light from the light source 110 is split by a splitter 102 into a sample beam and a reference beam which are respectively conveyed to the sample arm and the reference arm via respective optical fibers. In the sample arm, the sample beam enters a circulator 105, passes to a double-clad fiber coupler (DCFC) 108 via a single-mode (SM) fiber 106, and is delivered to the OCT probe 160 via a double clad fiber 107. In the OCT probe 160, the PIU 160 controls the sample beam to irradiate the sample 170 in a scanning manner. Light of the sample beam reflected and/or scattered by the sample 170 is collected by optics arranged at the distal end of probe 160, and the collected light transmitted back through the PIU 150 to DCFC 108. The DCFC 108 couples one part of the sample beam towards the circulator 105 via the SM fiber 106; and the circulator 105 guides the one part of the sample beam to the combiner 104. In addition, the DCFC 108 couples another part of the sample beam to a detector 122 (second detector) via a multi-mode fiber 109.

In the reference arm, light of the reference beam enters a circulator 103 and is delivered to the reflector 140 via a non-labeled optical fiber. In the case of Time Domain OCT imaging, the reflector 140 may be implemented as a scanning mirror. And, in the case of Frequency Domain OCT (FD-OCT) imaging, the reflector 140 may be implemented as a stationary mirror. Light of the reference beam reflected from the reflector 140 passes through the circulator 105, and is also guided to the combiner 104. In this manner, the sample and reference beams are combined at the beam combiner 104 and then detected by detector 121 to generate interference signals according to known OCT principles.

A fiber optic circulator (e.g., circulator 103 or 105 in FIG. 1) is a passive, polarization-independent, three-port device that acts as a signal router. Light from a first fiber is input to the circulator via a first port and directed to a second fiber via a second port. Light returning through the second fiber is redirected to a third fiber via a third port with virtually no loss. That is, light input into the first port is not directly coupled into the third port fiber, and light input into the second port is not coupled into the first port fiber. Therefore, the optical circulator (103 and 105) enables a low loss output of the sample and reference beams to obtain accurate interference patterns from the OCT interferometer.

The output of the OCT interferometer (interference patterns) obtained from combiner 104 is detected by the detector 121 (first detector). The first detector 121 is implemented as an array of photodiodes, a photo multiplier tube (PMT), a multi-array of cameras or other similar interference pattern detecting device. The signals output from the first detector 121 are pre-processed by data acquisition electronics (DAQ1) 131, and transferred to a computer 190. The computer 190 performs signal processing to generate OCT images in a known manner. The interference patterns are generated only when the path length of the sample arm matches the path length of the reference arm within the coherence length of the light source 110.

The second detector 122 detects a part of the sample beam output by the DCFC 108 via the multi-mode fiber 109, and outputs an analog signal corresponding to an intensity of the backscattered light (backscattered signal). The signal output from detector 122 is converted to digital data with data acquisition electronics (DAQ2) 132. Notably, as later explained more in detail, the digital signal corresponding to the intensity of the backscattered light is used as a trigger signal for starting and/or ending pullback and image recording. Therefore, the signal output from detector 122, and converted to digital data by data acquisition electronics (DAQ2) 132 can be used directly as a trigger signal or it can be transferred to the computer 190 for control processing.

In a typical medical imaging application, the components of the OCT probe 160 are the only components of the OCT system 100 that require to be contact with (or in close proximity to) the area of patient being imaged (e.g., a bodily lumen). Accordingly, the components of probe 160 are provided in the form of a handheld imaging probe or catheter, which is, typically, operated by a surgeon or other physician performing medical diagnosis or treatment. The OCT interferometer including light source 110, the detector unit 120, and data acquisition electronics 130 may be assembled into an imaging console located remotely from the OCT probe 160. Control signals for operation and communication between the console and the probe 160 are mainly originated from computer 190 and transferred to the probe 160 via the patient interface unit (PIU) 150.

<Use of Double Clad Fiber (DCF)>

Figure 2A:
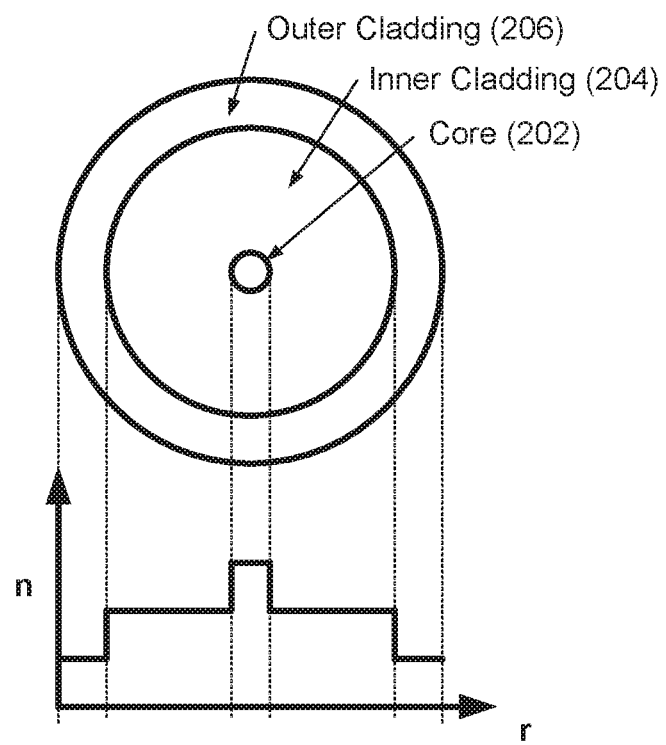
FIG. 2A shows a cross-sectional structure of a double clad fiber (DCF).
Figure 2B:
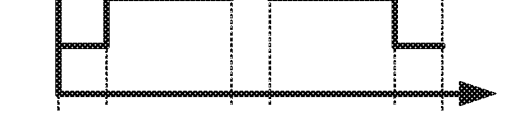
FIG. 2B shows an index of refraction distribution of a DCF.

The DCFC 108, PIU 150, and probe 160 are connected to each other by double clad fibers. In FIG. 1, DCFC 108 is connected to PIU 150 by a double clad fiber (DCF) 107-2. In addition, as explained more in detail below, the OCT probe 160 is connected to PIU 150 by a DCF 107-1. FIG. 2A shows a cross-sectional structure of a DCF 200 which consists of a core 202, an inner cladding 204, and an outer cladding 206 arranged concentrically in this order. Typical dimensions of commercially available double clad fibers used in OCT imaging are, for example, a 9 micron (μm) core diameter, 105 μm inner cladding diameter, and 125 μm outer cladding diameter. Light transmission in the core region is primarily single-mode, whereas in the inner cladding light transmission is multimode. The typical index of refraction (n) of a DCF for biomedical applications is decreasingly cascaded as a function of its radius (r) from the core center to the inner and outer cladding boundaries, as illustrated in FIG. 2B. The integration of both single-mode and multimode light transmissions in a single fiber allows the use of a single optical fiber for the delivery of illumination light (using the single-mode core) and the collection of the tissue-reflected light (using the multimode inner cladding).

Figure 2C:
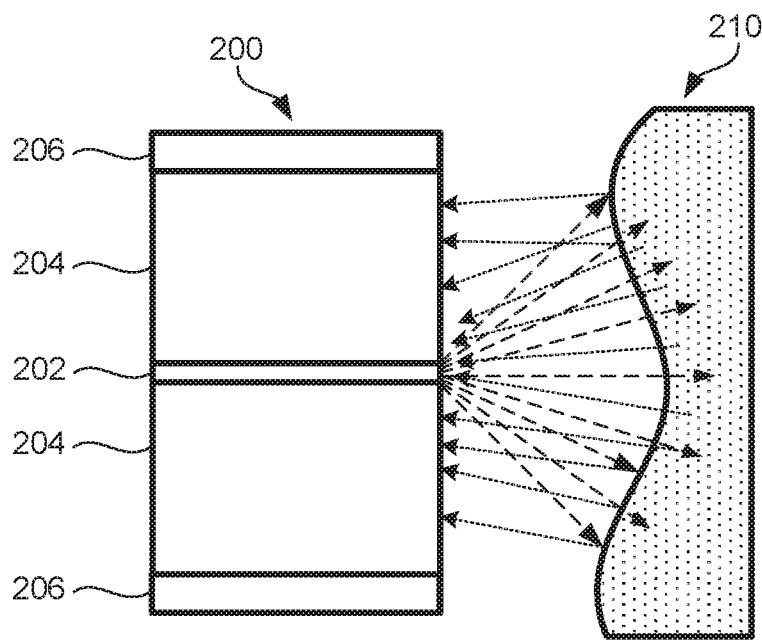
FIG. 2C shows irradiation and collection of light using a DCF.

In one embodiment of the present patent application, as illustrated in FIG. 2C, the OCT light (sample beam) illuminates a sample 210 through the core 202 of DCF 200. Upon interaction, light scattered and/or reflected from the sample 210 is collected by both the core 202 and the inner cladding 204. Thus, the backscattered light is delivered back through both the core 202 and the inner cladding 204 of DCF 200. Referring back to FIG. 1, since the probe 160, the PIU 150, and the DCFC 108 are interconnected via double clad fibers 107-1 and 107-2, the light backscattered from the sample is collected and conveyed back to DCFC 108.

The DCFC 108 has a function to separate light of the sample beam transmitted through core and clad. Specifically, the DCFC 108 is used for single fiber endoscopy by separating single-monde signals from multi-mode signals. Light in the core of the DCF 107-1 (core light) propagates through DCFC 108 with low loss and proceeds to the circulator 105 via single mode fiber 106. On the other hand, light in the clad of the DCF 107-1 (clad light) does not propagate through DCFC 108, but instead the DCFC 108 couples the clad light onto a multi-mode fiber 109. In this manner, only the clad light (light backscattered from the sample 170) is delivered to the second detector 122 through the multi-mode fiber 109.

The second detector 122 outputs an analog signal corresponding to the intensity of the clad light (backscattered light), and the signal output from detector 122 is converted into digital data by data acquisition electronics (DAQ2) 132. The digital data corresponding to the intensity of the backscattered light is then transferred to computer 190. Instead of using a double clad fiber connector (DCFC), the core light can be separated from the clad light with the use of optical filters and or beam splitters. For example, spatial filtering, such as a pinhole can be used to pass only core light to detector 121 while blocking clad light. Similarly, apodization (e.g., using an apodization mask) may be used to block the core light and pass only the clad light.

<Detection of Clad Light Intensity>

Figure 3A:
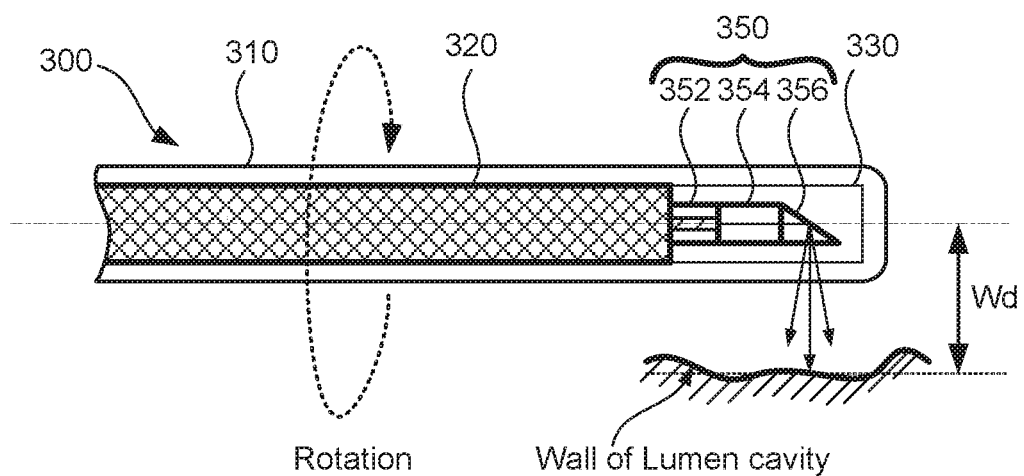
FIG. 3A illustrates an exemplary representation of an OCT probe (optical probe) usable in a catheter to image a sample.

The intensity of the backscattered light (intensity of clad light) detected by detector 122 depends on the distance between the catheter and the sample (generally known as the "working distance"). FIG. 3A illustrates an exemplary representation of an OCT probe (optical probe) usable in a catheter 300. The catheter 300 comprises a sheath 310, a coil 320, a transparent protector 330 and an optical probe 350. The distal end of the probe 350 includes a double clad fiber (DCF) 352, a lens 354 (e.g., a GRIN lens), and a reflecting surface 356. The catheter 300 is connected at the proximal end thereof to the PIU 150 (as shown in FIG. 1). The coil 320 delivers rotational torque from the proximal end to the distal end by a non-illustrated rotational motor located in the PIU 150. At the distal end of the probe 350, the reflecting surface 356 (e.g., a mirror or a prism) deflects the illumination light (sample beam) outward toward the sample (wall of the lumen cavity). The coil 320 is fixed with the optical probe so that a distal tip (distal end) of the optical probe also spins (rotates) to obtain an omnidirectional view of the inner surface of hollow organs (lumens), such as vessels. At the proximal end of the optical probe 350 the double clad fiber 352 is connected with the PIU 150 via a non-illustrated fiber connector. The double clad fiber 352 is used to deliver and collect OCT light through the core, and to collect backscattered light from the sample through the clad, as explained above. The lens 354 is used for focusing and collecting light to and/or from the sample, which is located at a working distance (Wd) from the center of the catheter. The intensity of backscattered light transmitted through the clad of DCF 352 is relatively higher than the intensity of backscattered light collected through the core because the size of the core is much smaller than the clad, as illustrated in FIGS. 2A-2C.

Figure 3B:
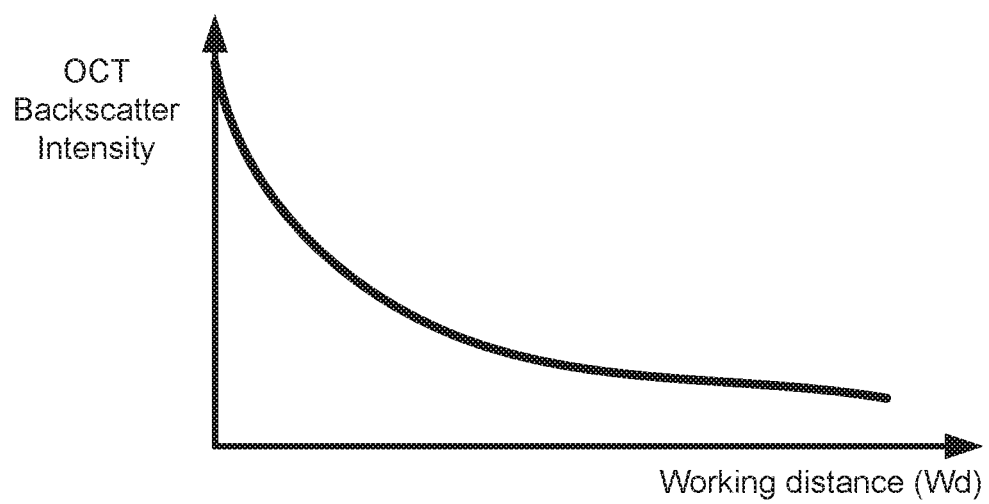
FIG. 3B is a graph illustrating a relationship of detected intensity of light backscattered from the sample as a function of the distance between the catheter and the sample (working distance).

FIG. 3B is a graph illustrating a relationship of detected intensity of light backscattered from the sample as a function of the distance between the catheter and the sample (working distance). As shown in FIG. 3B, the shorter the working distance is, the higher the detected intensity of the backscattered signal is because of collection efficiency of the catheter. There are various factors that can determine the collection efficiency. For example, the longer the working distance is, the smaller the solid angle from sample to active area of the optical probe is. Accordingly, the collection efficiency can be determined by the solid angle from sample to active area of the optical probe. The collection efficiency also depends on the optical parameters (focusing position, Numerical Aperture, spot size, etc.) of the OCT probe. Here, it should be noted that backscattered intensity also depends on the amount of scatterers interacting with the sample beam. For example, it is known from the dynamics of blood flow (hemodynamics) that the primary scatterers of light in intravascular examinations are red blood cells (RBCs). Therefore, the intensity of the backscattering signal can be monitored to determine the working distance (Wd) and the amount and/or density of a scattering medium (e.g., RBCs) surrounding the distal end of optical probe 350. Accordingly, the inventor(s) of the present patent application have recognized that it is possible to use the intensity of the backscattered signal to constantly monitor the state of clearance around the catheter, and to use the backscattered signal to trigger pullback and image recording in real-time and without having to first analyze, process or record images of the lumen cavity.

<Trigger Using Cladding Mode>

According to the present disclosure, in intravascular imaging, when blood is surrounded around the catheter, backscattering from the blood cells is detected as a high-intensity signal with the second detector 122. Then, when the blood cells are cleared by flushing media such as contrast agents, saline solution, and/or dextran, the signal received by the second detector 122 gradually drops off because the flushing media is relatively transparent, and because there is low backscattering due to lack of scattering media (red blood cells) surrounding the distal end of the catheter.

Figure 7:
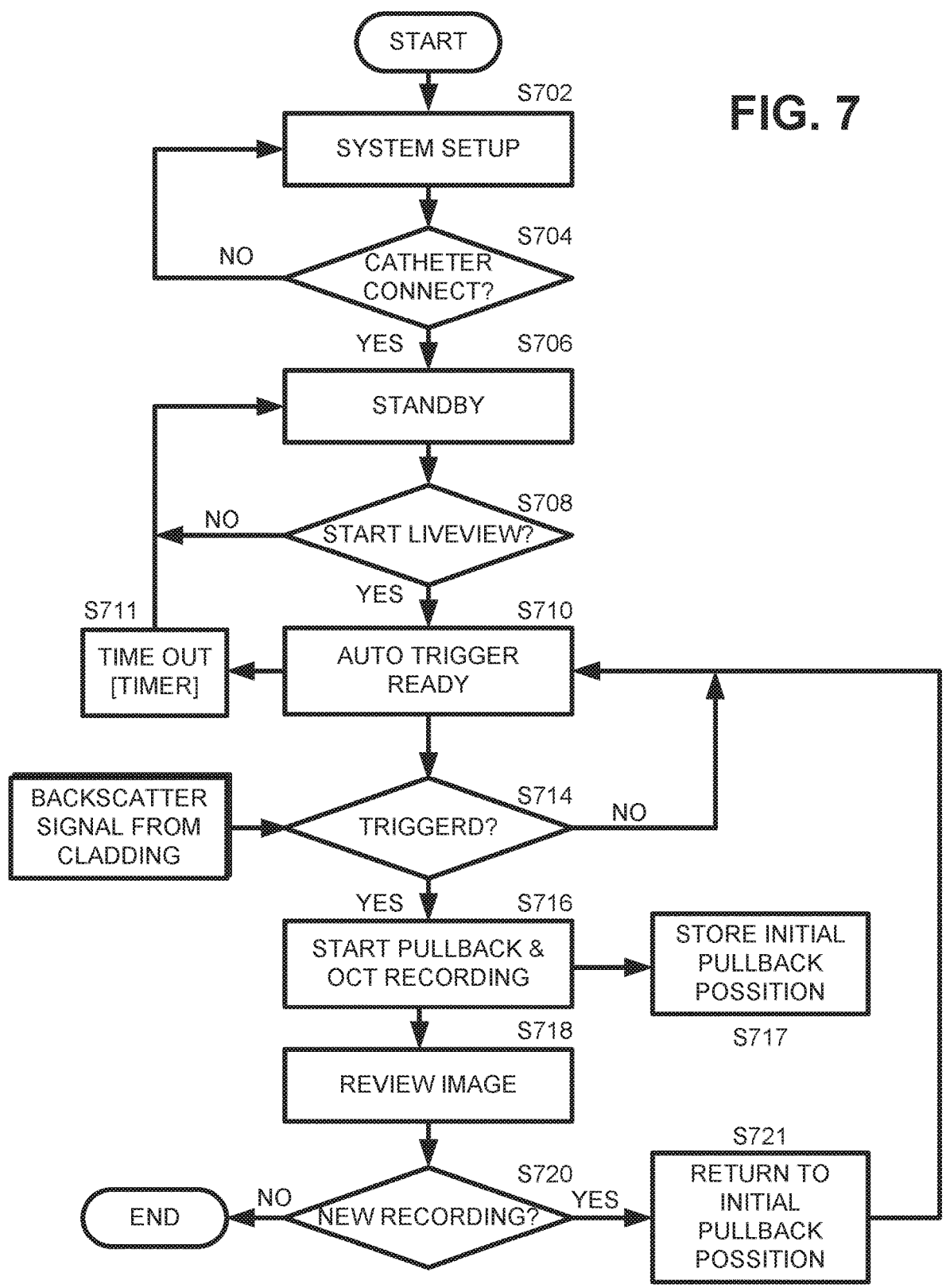
FIG. 7 is a flow process for controlling the OCT system to trigger pullback and image recording using backscattered signal.

According to some embodiments, the intensity of the backscattered light detected by detector 122 is constantly monitored during blood clearance. Then, when the signal crosses a certain threshold, the computer 190 generates a trigger signal to automatically start pullback and recording of OCT images. The time sequence for the trigger signal and initiation of pullback and recording is shown in FIGS. 4A through 4C, and a flow process for controlling the OCT system 100 is shown in FIG. 7.

Figure 4A:
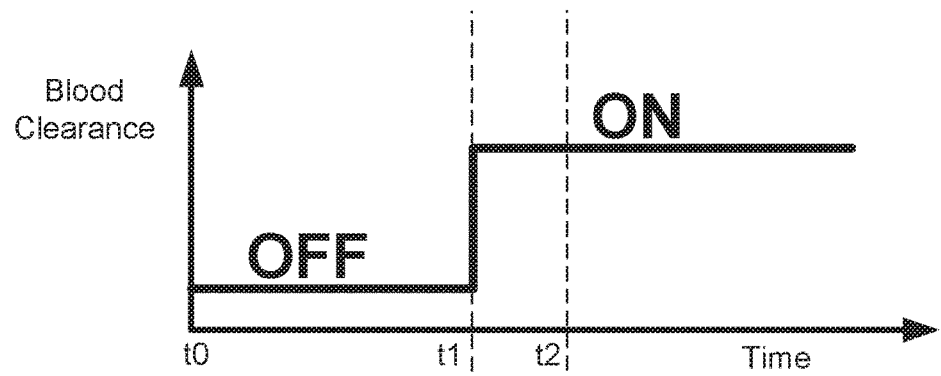
FIG. 4A illustrates a logic signal for initiating a "blood clearance" operation.
Figure 4B:
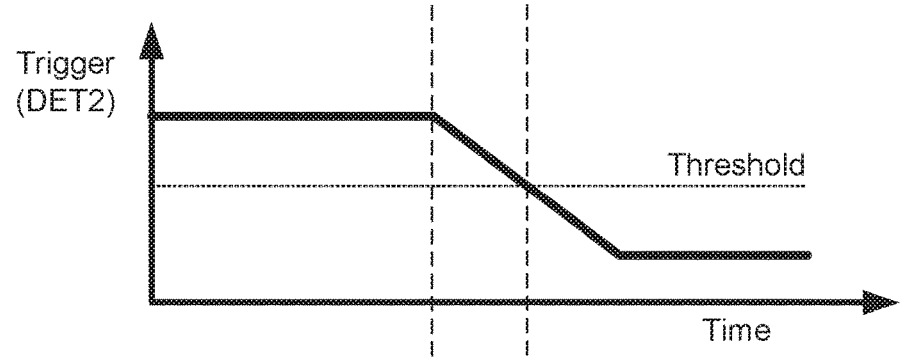
FIG. 4B illustrates a trigger signal based on backscattered intensity detected by second detector 122 and compared to a threshold.
Figure 4C:
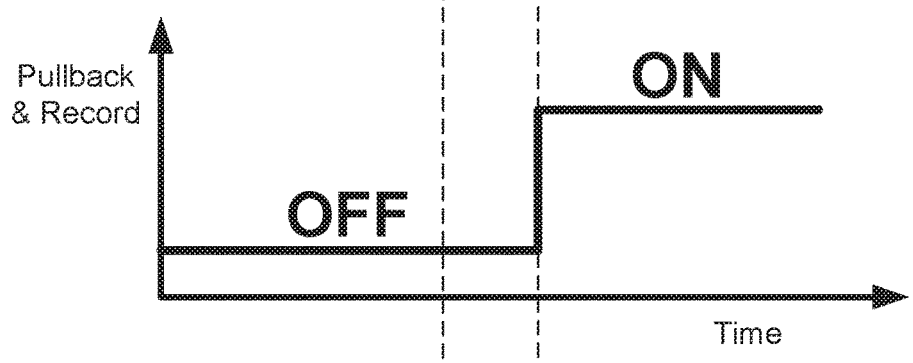
FIG. 4C illustrates a logic signal for initiating pullback and recording operations.

FIG. 4A illustrates a logic signal for initiating a "blood clearance" operation. FIG. 4B illustrates a trigger signal based on backscattered intensity detected by second detector 122 and compared to a threshold. FIG. 4C illustrates a logic signal for initiating pullback and recording operations.

As illustrated in FIG. 4A, at a time t0, the second detector (DET2) 122 detects a backscattering signal. At a time t1, a blood clearance operation is executed, for example, by an imaging practitioner (a user) while observing the location of the catheter with respect to a region of interest. Real-time observation of the region of interest may be performed by, for example, liveview imaging with catheter itself, or it may be performed with the use of a secondary imaging modality. Once a blood clearance operation is initiated (ON) at time t1, the detector 122 (DET2) continuously monitors the intensity of the backscattering signal until the level of backscattering signal reaches a predetermined threshold. FIG. 4B shows an exemplary graph of a signal seen at detector 122 (DET2). The signal of detector 122 is used as a trigger signal which is compared with a threshold. As shown in FIGS. 4A-4C, at a time t2, once the intensity of the backscattering signal reaches the predetermined threshold, the computer 190 automatically initiates pullback and image recording operations. For example, at time t2, the computer 190 controls the PIU 150 to effect the pullback operation, and controls the first detector 121 to record OCT images based on OCT interference signals. In this state (ON at time t2), the second detector 122 will continue monitoring the intensity of the backscattering signal such that if, for some reason, the intensity suddenly increases above the threshold, the pullback and recording can be automatically stopped to prevent recording of unnecessary (noisy) images.

<Pullback Operation>

Figure 5A:
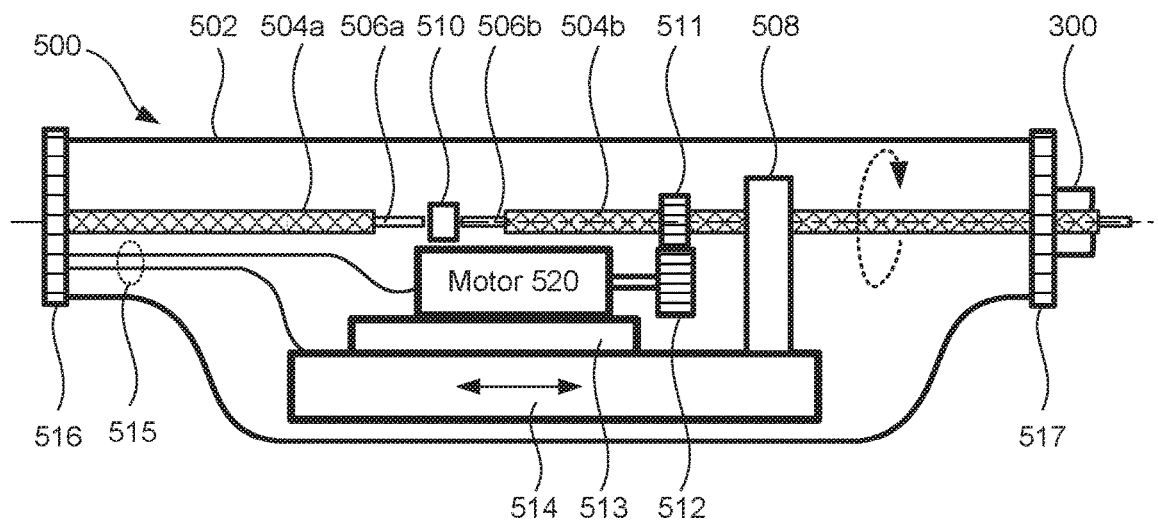
FIG. 5A schematically shows one exemplary implementation of relevant parts of a patient interface unit (PIU).

FIG. 5A schematically shows one exemplary implementation of relevant parts of a patient interface unit (PIU) 500 which is located at the proximal end of catheter 300 (shown in FIG. 3A). As shown in FIG. 5A, the PIU 500 is encased in an outer casing 502, which serves as a housing for mechanical, electronic, and optical components useful for control of the OCT optical probe. Also included in the housing 502 is a fiber optic rotary joint (FORJ) comprised of a rotational motor 520, a motorized translation stage 514, and free-space optical connections 510. At one end, the PIU 500 is provided with an optical/electrical connector 516, and at the other end thereof the PIU 500 is provided with an optical connector 518. A double clad fiber 506a encased in a sheath soda and electronic wiring connections 515 connect the PIU 500 to the sample arm of OCT interferometer and to computer 190 via the connector 516. A double clad fiber 506b encased in a sheath 504b are part of the catheter 300 and are connected to the PIU 500 via the connector 517. It is understood that other elements such as a guidewire and one or more conduits, e.g., for delivering a blood clearing medium (liquid), can be included in the catheter 300.

The motor 520 and motorized translation stage 513 provide rotational and translational torque for actuation of the movable components of catheter 300. Motor 520 drives a non-labeled shaft to rotate a gear 512 which transfers rotational torque to gear 511. The motor 520 is mechanically fixed to a base plate 513. In addition, a motorized translation stage 514 is also fixed to the base plate 513. The motorized translation stage 514 serves to provide translational torque for controlling linear movement (insertion into a lumen or pullback) of the movable components within catheter 300. A support 508 provides support and directional control for translational movement of the movable components within catheter 300. In other words, support 508 serves as a linear guide for translational movement. The motorized translation stage 514 is also used for providing translational torque during pullback. The connector 517 is a catheter connector to be connected to the catheter 300.

Rotational and translational torque for actuation of the movable components of catheter 300 is not limited to motorized movement. Instead of motors and mechanical gears, rotational and translational torque may also be implemented by using pneumatic or electromagnetic driving mechanisms to achieve rotary and forward/backward mechanical movement. See, for example, publication US 20140180133 (Brennan et al.), which is incorporated by reference herein in its entirety. In addition, ultrasonic motor (USM) systems may be advantageously used. For example, in a case of operating the OCT probe under the magnetic field of an MR-based modality, USM or pneumatic drive mechanisms can be used in the FORJ to avoid the effects that a magnetic field would have on metallic based driving mechanisms.

Figure 5B:
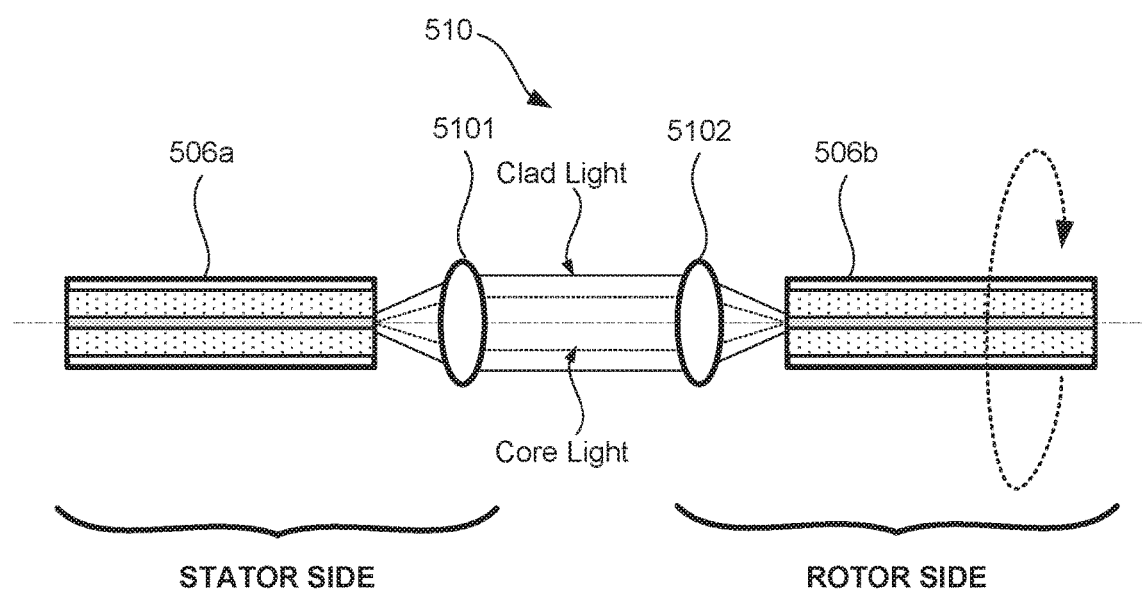
FIG. 5B shows an exemplary implementation of free-space optics used as optical connections in a fiber optic rotary joint (FORJ).

FIG. 5B shows a detailed view of an exemplary implementation of the catheter free-space optical connections 510 which are part of the FORJ. The catheter optical connections 510 include free space optics such as a pair of lenses 5101 and 5102. The FORJ allows uninterrupted transmission of an optical signal while rotating the double clad fiber on the right side (rotor side) along the fiber axis. The FORJ has a free space optical beam coupler to separate rotor and stator sides. The rotor and stator sides both comprise a double clad fiber 506 with a lens to ensure the light is transmitted as a collimated beam. The rotor side is connected to the catheter 300, and the stator side is connected to the optical subsystems within the PIU 500. The rotational motor 520 delivers the torque to the rotor or rotational side. It should be understood from FIG. 5B, that the lens 5101 needs not be separated from DCF 506a, and similarly lens 5102 needs not be separated from DCF 506b, as long as a collimated beam is transferred from the stator side to the rotor side and vice versa the lenses can be arranged at anywhere between DCF 506a and DCF 506b.

<System Control and Image Processing>

Figure 6:
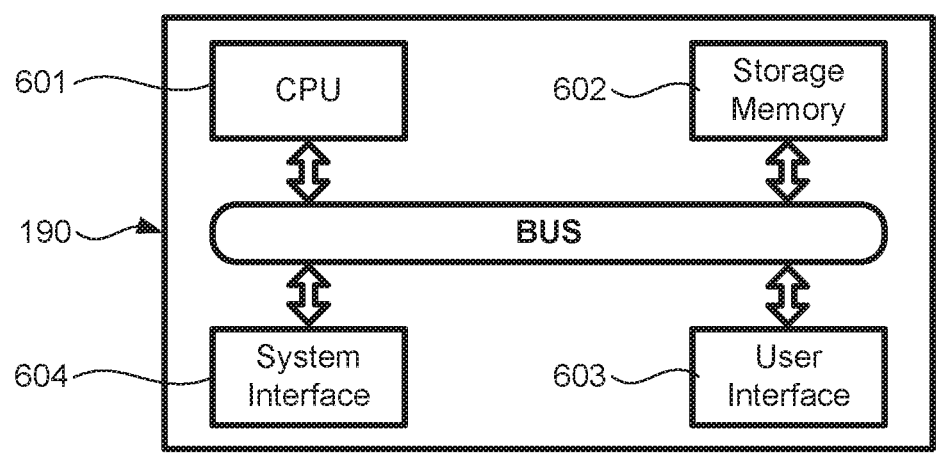
FIG. 6 is a block diagram of an exemplary computer control system for performing control and image processing in the interferometric OCT system 100.

FIG. 6 is a schematic diagram of an exemplary computer control system for the interferometric OCT system 100. As shown in FIG. 6, the computer control system is representative of computer 190 shown in FIG. 1. In FIG. 6, the computer 190 includes a central processing unit (CPU) 601, a storage memory (ROM/RAM) 602, a user input/output (I/O) interface 603, and a system interface 604. The various components of the computer 190 communicate with each other via a data bus (BUS) in a known manner.

Storage memory 602 includes one or more computer-readable and/or writable media, and may include, for example, a magnetic disc (e.g., a hard disk drive HHD), an optical disc (e.g., a DVD®, a Blu-ray®, or the like), a magneto-optical disk, semiconductor memory (e.g., a non-volatile memory card, Flash® memory, a solid state drive, SRAM, DRAM), an EPROM, an EEPROM, etc. Storage memory 902 may store computer-readable data and/or computer-executable instructions including Operating System (OS) programs, and control and processing programs.

The user interface 603 provides a communication interface (electronic connections) to input/output (I/O) devices, which may include a keyboard, a display, a mouse, a printing device, a touch screen, a light pen, an external optical storage device, a scanner, a microphone, a camera, a drive, communication cable and a network (either wired or wireless).

The system interface 604 also provides communication interfaces (electronic connections) for one or more of the light source 110, detectors 121-122, data acquisition electronics DAQ1 (131) and DAQ (132), and the patient unit interface (PIU) 150. The function of the user interface 603 and of the system interface 604 may be realized at least in part by computer executable instructions (e.g., one or more programs) recorded on storage 902. Moreover, the computer 190 may comprise one or more additional devices, for example, components such as a communications or network interface, a circuit interface (e.g., a field-programmable gate array: FPGA) to control one or more of the light source 110, detectors 121-122, mirror 140, and PIU 150.

The CPU 601 is comprised of one or more processors (microprocessors) configured to read and perform computer-executable instructions stored in the storage memory 602. The computer-executable instructions may include those for the performance of the novel processes, methods and/or calculations disclosed herein. For example, CPU 601 calculates the intensity backscattered light based on electric signals output from optical detectors 120 (121-122) and pre-processed by the acquisition electronics 130. In addition, CPU 190 calculates and/or determines initiation and termination of pullback and image recording based on the OCT scattering signal reaching a predetermined threshold, as described more in detail elsewhere in this disclosure.

FIG. 7 illustrates an exemplary flow process for controlling the imaging apparatus to trigger pullback and image recording based on the backscattering signal reaching a predetermined threshold. The process of FIG. 7 assumes an operational state in which a non-illustrated system console including computer 190 undergoes a system setup at steps S702 and S704. System console setup may include, for example, at step S702, executing a booting sequence of computer 190 and initializing the system software that operates the OCT system 100. In addition, system setup may include, at step S704, the computer 190 detecting whether a catheter is connected to the system console. When the catheter is connected, the computer 190 may issue commands to also initialize certain parameters of the catheter and the optics connected to it. For example, the computer 190 may enable the electronic elements of PIU 150, the detector 120, DAQ 130 and light source 110.

After the system detects that a catheter is connected to the system console (S704: YES) and the system is initialized, the process advances to step S706. In step S706, the system enters a "standby mode". In the standby mode, the entire imaging system is enabled and ready for operation, but catheter movement (rotation and translation) is not yet activated. At step S708, the system may start to obtain real time images (liveview images) of the environment surrounding the catheter (S708: YES) but without recording such liveview images, or the system remains in standby mode (S708: No) until real time observation is started. In the event that liveview observation does start, the process advances to step S710.

In step S710, the system enters an "auto trigger ready" mode. Specifically, at step S710, the imaging system can initiate rotation and translation movement of the imaging optics within the catheter, and the system can be used to observe liveview images while operating the catheter within a patient to determine whether a region of interest is reached. In the auto trigger mode, the system may initiate a "time out" timer at step S711. If the time-out timer expires, the system stops the movement of the imaging optics and stops the liveview imaging, and then returns to the standby mode (S706). On the other hand, once the auto trigger mode is achieved, at step S714, the system awaits for a determination of whether a trigger signal is received.

Backscattered signals detected by the second detector 122 are analyzed to average multiple a-lines and/or frames while the catheter rotates (spins) without recording any OCT images. Signals from at least all a-lines within a frame may be averaged in order to detect backscattering from an omnidirectional view of the inner surface of hollow vessels to establish a state of blood clearance around the distal end of the catheter. In this manner, it is possible to prevent the generation of a trigger with a partial blood clearance, and also to reduce the influence of noise artifacts. Reliable trigger is achieved with this processing.

At step S714, the computer 190 analyzes the trigger signal received from the cladding mode of the DCF 506 based on the intensity of the backscattered signal detected by detector 122. More specifically, at step S714, the computer 190 receives the signal output from second detector 122, and monitors the intensity of the received signal to compare such intensity with a predetermined intensity threshold, as shown in FIG. 4B. The threshold value, which corresponds to an intensity level of the backscattered signal, can be determined experimentally based on a variety of parameters.

As illustrated in FIG. 3B, the intensity level of the backscattered signal can be calculated as a function of the working distance between the distal end of the probe and an inner wall of the bodily lumen such that as the working distance increases the intensity level decreases. Therefore, one aspect that can determine the intensity level of the backscattered signal may be the radius of the bodily lumen (e.g., radius of a vessel). However, the intensity of the scattering signal is also affected by the concentration of light scatterers (blood cells) existing in the fluid (blood) contained in the bodily lumen. Since concentration of blood cell count in a vessel can vary according to a subject's health condition, the initial intensity of the backscattering signal could take into consideration the blood cell count of each individual being examined. In this manner, when blood vessel flushing with a clear medium is applied, the threshold may be adjusted to ensure a minimum amount of clearance. In one embodiment, the threshold may be established as a point in time when the intensity of the backscattering signal decreases to a 75% of its initial (maximum) intensity level. The threshold may also be established as a function of time to ensure that the probe scans at least a full 360 degree view of the vessel and the pullback of the probe can travel at least a predetermined distance. For this reason, the trigger signal can occur after a short delay after initiating a clearance operation, but such delay cannot be long because a clearance state may not be maintained longer than a few milliseconds. The threshold may also be established as a function of detected signal fluctuation. During transition from blood to flush media, the detected signal becomes fluctuated so that system can detect when flush starts and becomes stable. Also, it is possible to combine multiple thresholds to make the system more reliable.

Once the intensity of the backscattered signal reaches the predetermined threshold, the computer 190 automatically outputs a command or signal (trigger signal) to the PIU 150 to initiate pullback of the probe, and at the same time computer 190 initiates image recording operations (S714: YES). That is, at step S714, after comparing the backscattering signal to the threshold value, pullback and image recording have been automatically triggered. Therefore, the flow process of FIG. 7 advances to S716 according to a time diagram illustrated in FIG. 4C. In the event that, at step S714, the backscattering signal detected by detector 122 does not reach the predetermined threshold (NO in S714), the system remains in auto trigger ready mode (i.e., the flow returns to S710). In this manner, the system will be eventually either timed out at S711 or automatically triggered (YES at S714) and then advance to S716.

At step S716, the system simultaneously starts catheter pullback and image recording. In addition, once the pullback and recording have been automatically triggered, the system may store the location at which the pullback started. That is, at step S717, the computer 190 can store the initial pullback position.

At step S716, OCT signals detected with the second detector 122 are processed and recorded to see at least a full omnidirectional view of the inner surface of hollow vessels. To that end, the pullback and image recording of step S716 are carried out for at least a length of time necessary to obtain a full 360 degrees of helical scanning of the region of interest being imaged. Here, it should be appreciated that pullback and image recording of step S716 can continue for as long as the "lumen cleared" state is maintained. Therefore, the computer 190 can continuously monitor the backscattering signal of detector 122 and compare it to the threshold. In this manner, at a point in time when the intensity of backscattering signal no longer meets the desired parameters of the threshold, the pullback and recording can be automatically ended to prevent the recording of non-useful image data.

Once the desired region of interest has been scanned at least a full 360 degrees, computer 190 can generate and output an OCT image of the region of interest for visual review. That is, the process advances to step S718 where image review is performed either visually by an imaging technician, by image processing carried out by the computer 190, or a combination of visual and image processing analysis. At step S720, either the imaging technician or the computer software can determine if a new recording should be performed. If a new recording should be performed (S720: YES), the process advances to step S721. At step S721, the computer 190 issues a command to PUI 150 to return (reset) the moving parts of the catheter to the initial pullback position (which was recorded at step S717). From step S721, the flow process can return to step S710 and enter again the auto trigger ready mode. Alternatively (optionally), the process can return to step S706 and enter the standby mode. After image review, when no further recording is required (S720: NO), the process and control of the imaging apparatus ends automatically or by manual operation.

<Multimodality With Fluorescence>

According to other embodiments, the OCT system includes a fluorescence subsystem. That is, some embodiments disclose a multi-modality imaging system. In these embodiments, the OCT system is the same as that described above. In the fluorescence subsystem a light 4 is excitation light illuminating the sample via the optical probe, and light 5 is fluorescence light collected by optical probe from the sample, and propagated to a third detector through the clad of the DCF. Here, a trigger signal is generated based on detected intensity of light 3 signals in order for a processor to control an operation of the catheter and record OCT images and fluorescence images.

Figure 8:
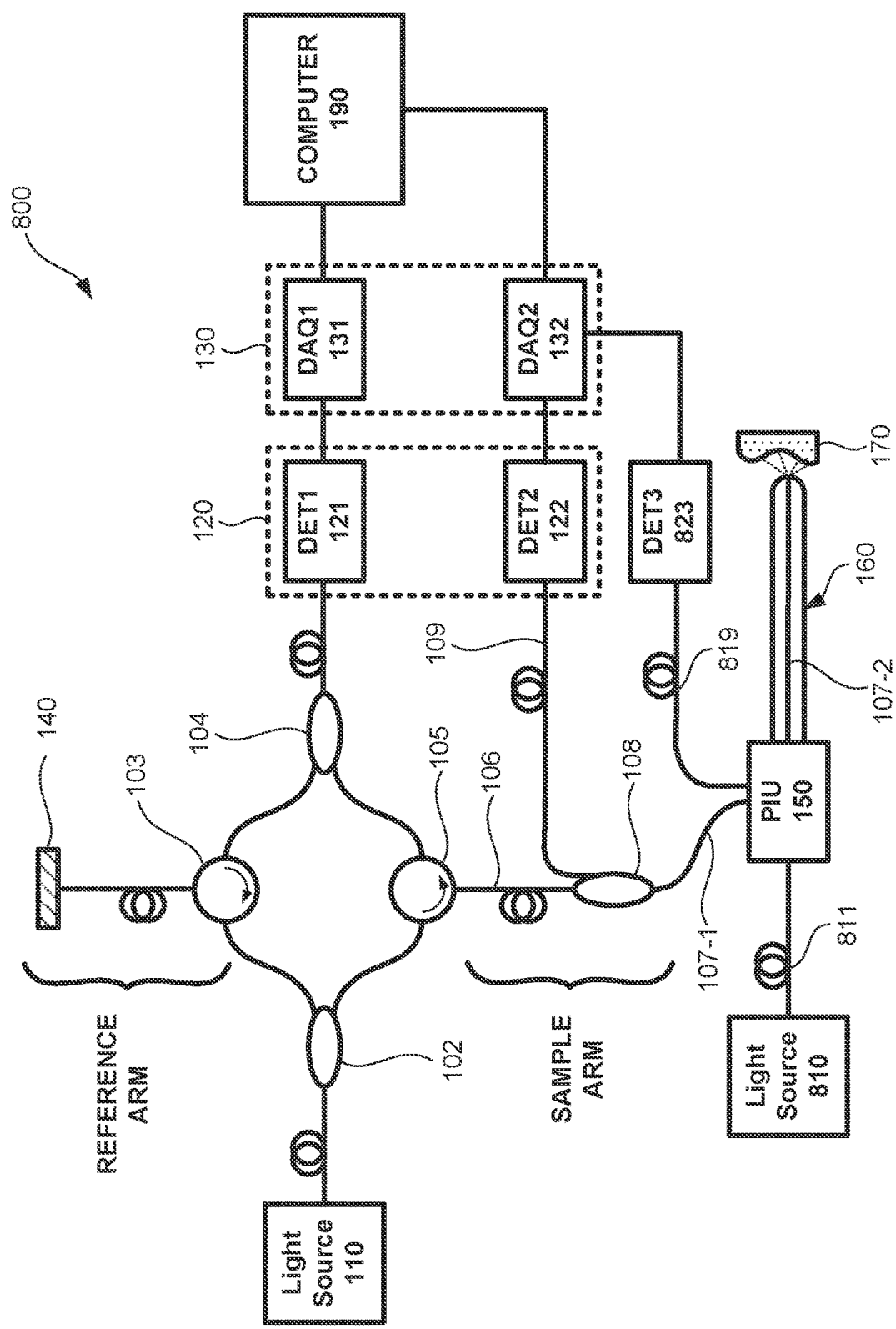
FIG. 8 is a functional block diagram of an OCT imaging system including a fluorescence subsystem according to some embodiments.

FIG. 8 illustrates an OCT imaging system 800 including a fluorescence subsystem. Imaging of coronary arteries by intravascular multi-modality OCT system is described. Specifically, in these embodiments, the system is able to detect blood clearance and start measurements automatically based on backscattered light by blood cells of a live subject (sample). This method does not require real-time processing of OCT or other modality's images. Therefore, an OCT imaging system including a fluorescence subsystem can achieve high-speed pullback and image recording trigger in real-time.

According to the embodiment illustrated in FIG. 8, the OCT imaging system 800 is similar to the OCT system 100 of FIG. 1. However, some embodiments include a fluorescence subsystem in addition to the OCT system 100. The fluorescence subsystem includes, but is not limited to, a light source 810 (third light source) and a detector 823 (third detector DET3), both respectively connected to PIU 150 via optical fibers 811 and 819.

An excitation light with a wavelength of 633 nm from a second light source 810 delivers to the sample 170 through the PIU 150 and the OCT probe 160. The sample 170 emits auto-fluorescence with broadband wavelengths of 633 to 800 nm, in response to being irradiated by the excitation light. The auto-fluorescence light is collected with the catheter and delivered to a third detector 823 (DET3) via an optical fiber 819 connected to the PIU 150. The signal output from detector 823 is digitized by data acquisition electronics 132 (DAQ2) and transmitted to computer 190.

The PIU 150 comprises a free-space optical beam combiner/splitter (e.g., dichroic filters) which separates the OCT light of around 1300 nm, from excitation light of 633 nm, and fluorescence light of 633-800 nm. Light having a wavelength of around 1300 nm is used to generate OCT images by core light and to generate a trigger signal by clad light. The process for generating a trigger signal based on backscattered signals in the multimodality embodiments is similar to the process described with respect to the embodiments described above.

Once computer 190 detects a trigger signal with the detector 122 (DET2), the second light source 810 turns ON, and the pullback and OCT recordation operations automatically initiate. In this manner, the multimodality system including the OCT imaging system 800 and the fluorescence subsystem can illuminate the sample with excitation light only during OCT recording. Fluorescence light is generally decayed with illuminated time because of photo-bleaching effect. Accordingly, it is desirable to illuminate the sample 170 with excitation light only during actual OCT measurement and recording of OCT images. To that end, the control of the second light source 810 is used with the driver and/or controller of the light source 810 and/or a shutter somewhere in between the light source 810 and the catheter, based on the trigger signal. The system of FIG. 8 can be advantageously used to simultaneously perform 3D OCT and near-infrared fluorescence imaging (NIRF) intravascular imaging to simultaneously visualize the physical status of vessel walls while analyzing flourochrome response of biological markers. In this manner, the trigger signal can also be used to more easily co-register the OCT images and fluorescence images with each other.

Figure 9:
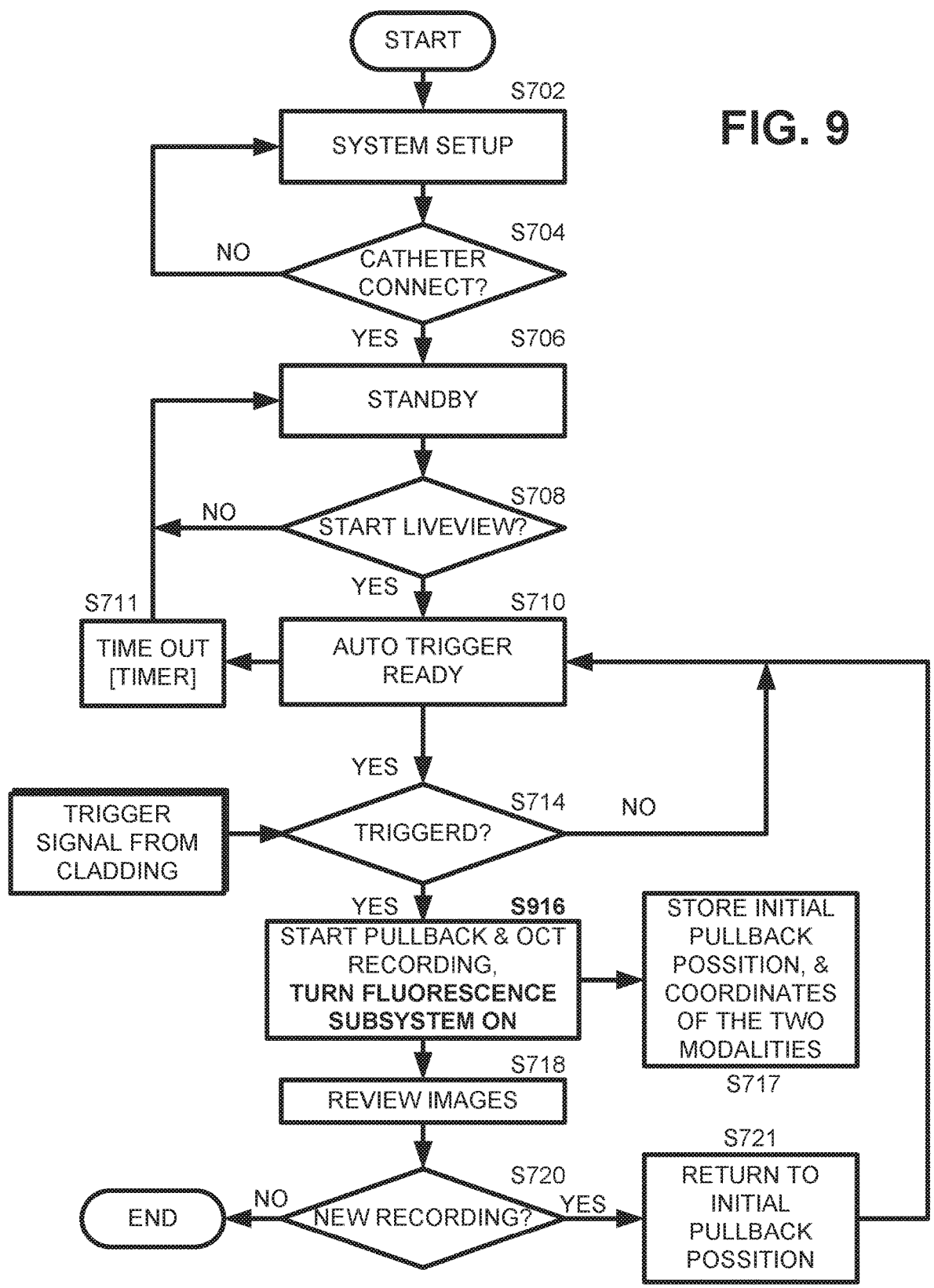
FIG. 9 illustrates an exemplary flow process for controlling the OCT imaging system including a fluorescence subsystem to trigger pullback, OCT image recording, and fluorescence imaging, based on a backscattering signal.

FIG. 9 illustrates an exemplary flow process for controlling the multi-modality imaging apparatus to trigger pullback, OCT image recording, and fluorescence imaging, based on the backscattering signal reaching a predetermined threshold. The threshold for the multi-modality system 800 is the same as that of FIGS. 4A-4C. The flow process of FIG. 9 is similar to the flow process of FIG. 7 except for step S916. In FIG. 9, at step S916, OCT signals detected with the second detector 122 are processed and recorded to see at least a full omnidirectional view of the inner surface of hollow vessels. In addition, at step S916, the light source 810 of fluorescence subsystem is turned ON, and fluorescence signals are recorded by detector 823 (DET3). Similar to the previous embodiment, the pullback, OCT recording, and fluorescence image recording of step S916 are carried out for at least a length of time necessary to obtain a full 360 degrees of helical scanning of the region of interest being imaged. Once the desired region of interest of the sample has been scanned at least a full 360 degrees, computer 190 can generate and output OCT and fluorescence images of the region of interest for visual review at step S718. Advantageously, at step S717 of this embodiment, in addition to recording the initial pullback position of the catheter, the system may also record the parameters and coordinates of the catheter (coordinates of the two modalities) with respect to sample, so that the OCT images and fluorescence images can be easily co-registered with each other without having to adjust for fluorescence decay time or photo-bleaching effects.

<Modifications>

Figure 10A:
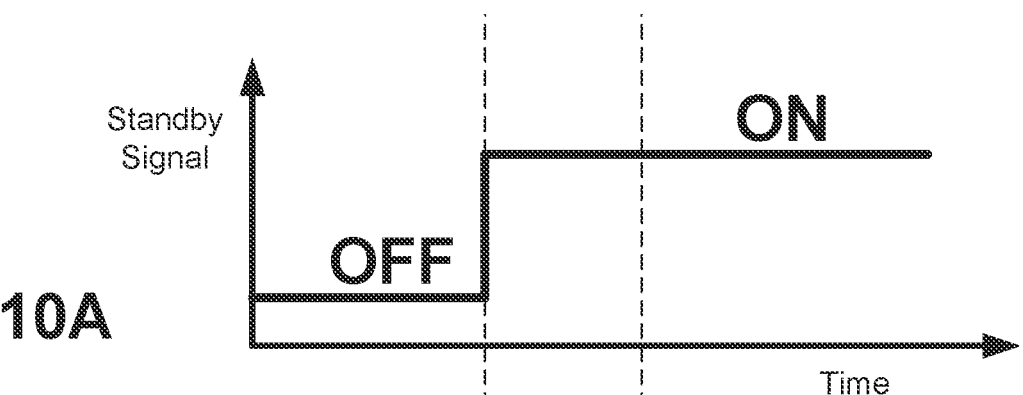
FIG. 10A illustrates a logic signal of a standby signal.
Figure 10B:
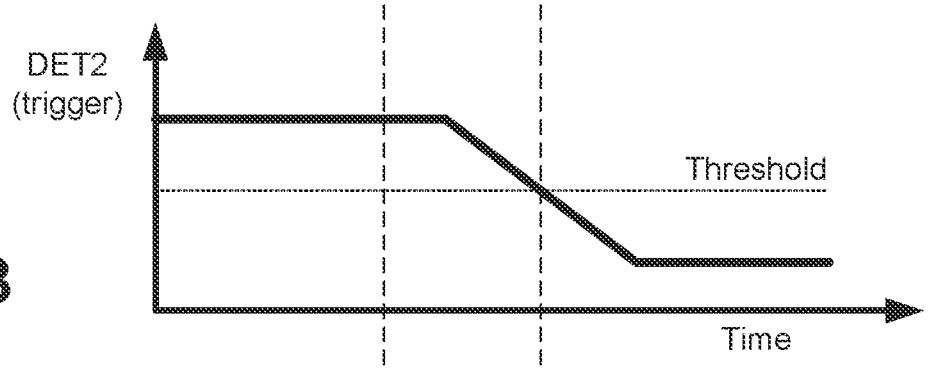
FIG. 10B illustrates a trigger signal based on backscattered intensity and compared to a threshold value.
Figure 10C:
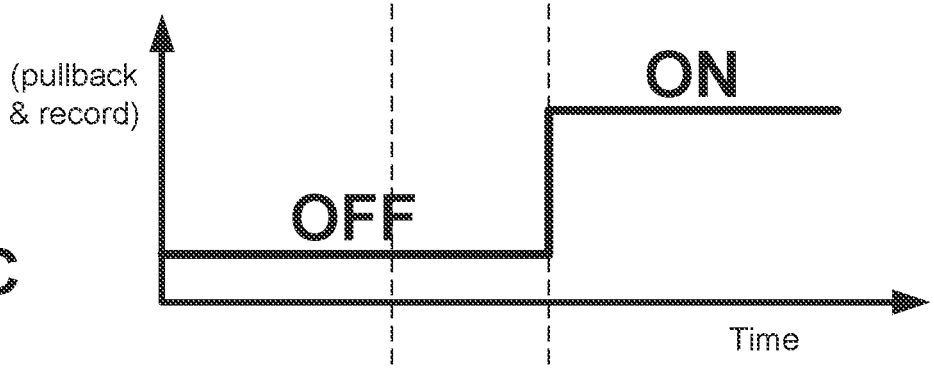
FIG. 10C illustrates a logic signal for initiating pullback, OCT image recording, and fluorescence imaging operations.

FIGS. 10A, 10B, and 10C illustrate a modified time sequence for the trigger signal and initiation of pullback and image recording. FIG. 10A illustrates a logic signal of a standby signal. FIG. 10B illustrates a trigger signal based on backscattered intensity detected by second detector 122 and compared to a threshold value. FIG. 10C illustrates a logic signal for initiating pullback and OCT image recording, and for initiating fluorescence imaging operations. In contrast to FIG. 4A where trigger signal (FIG. 4B) is time-synchronized with the logical ON of the clearance state, the logical ON of FIG. 10A does not need to be time-synchronized with the trigger signal of FIG. 10B. The reason for this is that, in FIG. 10A, the auto trigger ready signal can be generated directly from the computer, e.g., manually.

The time sequence and logic signals of FIGS. 10A-10C can be equivalently applied to the systems of each of the embodiments described herein. With the modified time sequence of FIGS. 10A-10C, the system is capable to generate a trigger signal only when another "auto trigger ready signal" (or "ready mode" signal) is ON, and the backscattered signal detected by detector 122 has crossed the threshold value. The devices such as light sources, shutters, computer, and/or motors starts by receiving the trigger.

Figure 11A:
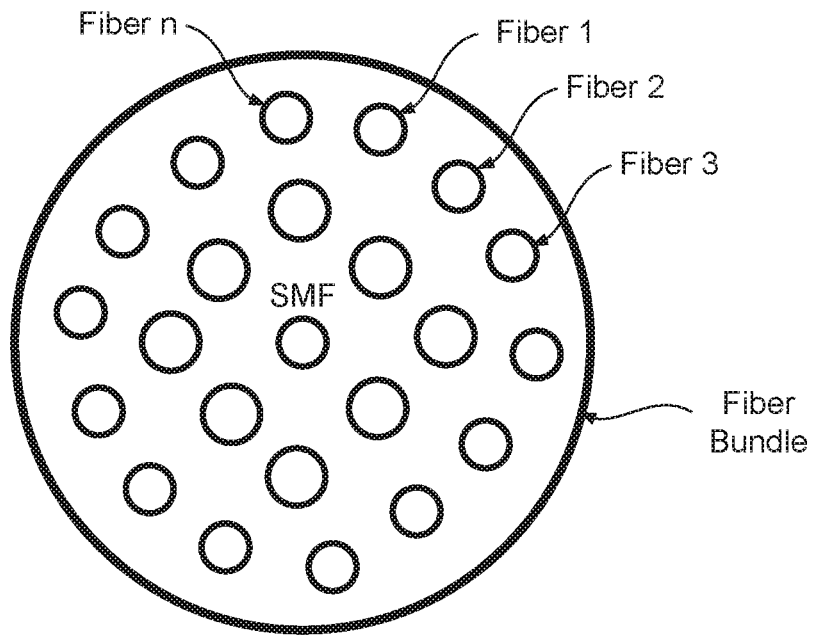
FIG. 11A shows a cross-sectional view of an exemplary fiber bundle.
Figure 11B:
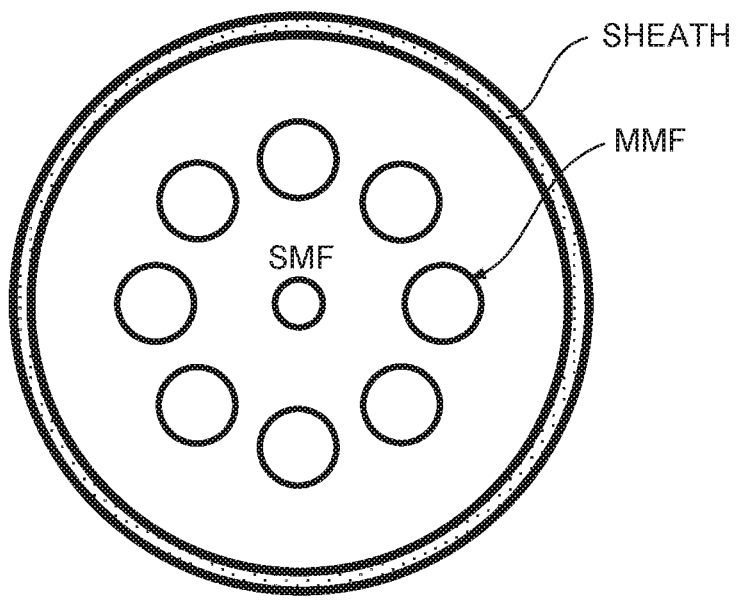
FIG. 11B show the cross-section of a multi-fiber structure.

As described above, the catheter includes a single double clad fiber (DCF) for delivering and collecting light to and from the sample. However, the catheter can be modified to include a fiber having more than two claddings (a multi-cladding fiber), or a fiber bundle, or a holey fiber (a photonic crystal microstructure fiber), or a custom-made multi-fiber structure, or combinations thereof. FIG. 11A shows a cross-sectional view of an exemplary fiber bundle, and FIG. 11B shows a multi-fiber structure. In both FIGS. 11A and 11B, a center fiber is a single mode fiber (SMF) used for collecting the OCT signal, while the plurality of fibers (Fiber 1, Fiber 2, Fiber 3 . . . , Fiber n) surrounding the center fiber are either multimode fibers (MMF) or single mode fibers used for collecting the backscattering light whose intensity signals are used for trigger of pullback and image recording.

While the present patent application has been described with reference to exemplary embodiments, it is to be understood that the invention is not limited to the disclosed exemplary embodiments. The scope of the following claims is to be accorded the broadest interpretation so as to encompass all possible modifications and equivalent structures and functions. To that end, it must be noted that the terminology used herein is for the purpose of describing particular embodiments only and is not intended to be limiting, unless so claimed. As used herein, the singular forms "a", "an", and "the", are intended to include the plural forms as well, unless the context clearly indicates otherwise. It should be further understood that the terms "includes" and/or "including", when used in the present specification and claims, specify the presence of stated features, integers, steps, operations, elements, and/or components, but do not preclude the presence or addition of one or more other features, integers, steps, operations, elements, components, and/or groups thereof not explicitly stated.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

What is claimed is:

1. An optical coherence tomographic (OCT) imaging system, comprising:
    an interferometer including a reference arm which transmits a reference beam and a sample arm which transmits a sample beam;
    a probe optically connected to the sample arm and configured to be inserted into a lumen to irradiate the lumen and/or a fluid contained within the lumen with light of the sample beam;
    a first detector in optical communication with the reference arm and the probe, the first detector configured to detect patterns of interference of light of the sample beam reflected and/or backscattered from the lumen and interfering with light of the reference beam to generate OCT interference signals;
    a second detector in optical communication with the probe and configured to detect an intensity of light of the sample beam backscattered by the fluid contained in the lumen to generate a backscattered intensity signal; and a processor operatively connected to the first and second detectors and configured to control pullback of the probe based on the backscattered intensity signal, wherein the probe is in optical communication with the first detector and the second detector via a first double clad fiber which has a core, an inner cladding and an outer cladding, wherein the first double clad fiber transmits the light reflected and/or backscattered by the lumen to the first detector as core light transmitted via core mode through the core, and transmits the light backscattered by the fluid contained in the lumen to the second detector as clad light via cladding mode by blocking the core light and passing only the clad light through the inner cladding and/or the outer cladding, wherein the processor, based on the backscattered intensity signal output by the second detector reaching a predetermined threshold value, automatically triggers pullback of the probe through the lumen and automatically initiates recording of the OCT interference signal without analyzing or processing OCT images of the lumen, and wherein the backscattered intensity signal output by the second detector corresponds to a concentration of light scatterers dispersed in the fluid contained in the lumen and being cleared from around the probe.

2. The OCT imaging system according to claim 1, wherein the lumen includes a bodily lumen comprised of a blood vessel, or a coronary artery, or a bodily cavity, wherein the predetermined threshold value corresponds to an intensity level of the backscattered signal calculated as a function of a working distance between a distal end of the probe and an inner wall of the bodily lumen such that as the working distance increases the intensity level decreases according to the concentration of light scatterers existing in the fluid contained in the bodily lumen, and wherein the processor is further configured to:
determine a clearance state indicative of a clearance of the light scatterers around the distal end of the probe,
compare the backscattered intensity signal to the predetermined threshold value, and
determine that the intensity level of the backscattered signal has decreased to at least 75% of a maximum intensity level.

3. The OCT imaging system according to claim 1, further comprising:
a patient interface unit (PIU) operatively arranged in the sample arm between the first double clad fiber and the probe,
wherein the PIU includes a catheter connector and a fiber optic rotary joint (FORJ) having a rotational motor and a translational stage,
wherein the probe includes a catheter which comprises a second double clad fiber and a torque coil disposed in a protective sheath,
wherein the catheter connector of the PIU is connected to the catheter, and
wherein the FORJ is configured to provide uninterrupted transmission of an optical signal between the sample arm and the catheter while rotating the second double clad fiber within the catheter.

4. The OCT imaging system according to claim 3, wherein the FORJ includes a free-space optical beam coupler configured to provide the uninterrupted transmission of an optical signal between the sample arm and the catheter,
wherein the first double clad fiber connecting the probe to the sample arm connects the sample arm to the PIU, and
wherein the FORJ is configured to provide the uninterrupted transmission of an optical signal between the sample arm and the catheter while rotating the second double clad fiber within the catheter and without rotating the first double clad fiber.

5. The OCT imaging system according to claim 3, wherein the probe irradiates the bodily lumen and the fluid contained within the bodily lumen with light of the sample beam transmitted through the core of the first double clad fiber,
wherein the probe collects the light backscattered by the bodily lumen and by the fluid contained in the bodily lumen through the inner cladding of the first double clad fiber, and
wherein the second detector detects the backscattered light transmitted through the inner cladding of the first double clad fiber.

6. The OCT imaging system according to claim 5, wherein the probe scans an inner wall of the bodily lumen in a helical path and collects the light backscattered from the inner wall of the bodily lumen through the second double clad fiber while the FORJ rotates and translates the second double clad fiber within the catheter.

7. The OCT imaging system according to claim 2, further comprising:
a first light source in optical communication with the sample arm and the reference arm, the first light source configured to emit light in a wavelength appropriate for irradiating the bodily lumen,
wherein the probe irradiates the bodily lumen and the fluid contained within the bodily lumen with the light emitted by the first light source.

8. The OCT imaging system according to claim 7, further comprising:
a second light source configured to irradiate the bodily lumen and the fluid contained within the bodily lumen with excitation light having a wavelength appropriate to produce auto-fluorescence from fluorescent biomarkers added to the fluid contained within the bodily lumen; and
a third detector configured to detect fluorescent light collected from the fluorescent biomarkers added to the fluid contained within the bodily lumen;
wherein the processor is further configured to, based on the backscattered intensity signal reaching the predetermined threshold value, automatically initiate recording of fluorescence images of the bodily lumen.

9. The OCT imaging system according to claim 8, wherein the first light source is low coherence light source that emits light with a center wavelength of about 1300 nm, and the second light source emits excitation light with a wavelength of about 633 nm, and
wherein the third detector is configured to detect fluorescent light with wavelengths in a range of about 633 nm to 800 nm.

10. A method for performing optical coherence tomographic (OCT) imaging with an interferometer including a reference arm which transmits a reference beam and a sample arm which transmits a sample beam, the method comprising:

inserting an OCT probe into a lumen containing a fluid, and irradiating the lumen and/or the fluid contained within the lumen with light of the sample beam;

detecting, using a first detector, patterns of interference of light of the sample beam reflected and/or backscattered from the lumen and interfering with light of the reference beam to generate OCT interference signals; and detecting, using a second detector, intensity of light of the sample beam backscattered by the fluid contained in the lumen to generate a backscattered intensity signal; and controlling, using a processor, (a) pullback of the probe based on the backscattered intensity signal and (b) recording of the OCT interference signals, wherein the probe is connected to the first detector and the second detector via a first double clad fiber which has a core, an inner cladding, and an outer cladding, wherein the first double clad fiber transmits the light reflected and/or backscattered from the lumen to the first detector as core light transmitted in core mode via the core, and transmits the light backscattered by the fluid contained in the lumen to the second detector as clad light in cladding mode by blocking the core light and passing only the clad light via the inner cladding and/or the outer cladding, and wherein the processor, based on the backscattered intensity signal reaching a predetermined threshold value, automatically triggers pullback of the probe through the lumen and automatically initiates recording of the OCT interference signals without analyzing or processing OCT images of the lumen, and wherein the backscattered intensity signal output by the second detector corresponds to a concentration of light scatterers dispersed in the fluid contained in the lumen and being cleared from around the probe.

11. The method of performing OCT imaging according to claim 10, wherein the lumen includes a bodily lumen comprised of a blood vessel, or a coronary artery, or a bodily cavity, the method further comprising:
calculating the predetermined threshold value corresponding to an intensity level of the backscattered signal as a function of a working distance between a distal end of the probe and an inner wall of the bodily lumen such that as the working distance increases the intensity level decreases according the concentration of light scatterers existing in the fluid contained in the bodily lumen, determining a clearance state indicative of a clearance of the light scatterers around the distal end of the probe, comparing the backscattered intensity signal to the predetermined threshold value, and determining that the intensity level of the backscattered signal has decreased to at least 75% of a maximum intensity level.

12. The method of performing OCT imaging according to 10, further comprising:

irradiating the bodily lumen and the fluid contained within the bodily lumen with excitation light having a wavelength appropriate to produce auto-fluorescence from fluorescent biomarkers added to the fluid contained within the bodily lumen; and detecting, with a third detector, fluorescent light collected from the fluorescent biomarkers added to the fluid contained within the bodily lumen; and processing the detected fluorescent light, in response to the backscattered intensity signal reaching the predetermined threshold value, to automatically initiate recording of fluorescence images of the bodily lumen.

* * * * *